United States Patent
Badens et al.

(10) Patent No.: US 10,494,587 B2
(45) Date of Patent: Dec. 3, 2019

(54) CONTINUOUS PROCESS FOR FRACTIONATING A SUSPENSION

(71) Applicants: Universite d'Aix-Marseille, Marseilles (FR); Centre National de la Recherche Scientifique, Paris (FR); Ecole Centrale de Marseille, Marseilles (FR)

(72) Inventors: Elisabeth Badens, Marseilles (FR); Christelle Crampon, Marseilles (FR)

(73) Assignees: Centre National de la Recherche Scientifique, Paris (FR); Universite d'Aix Marseille, Marseilles (FR); Ecole Centrale de Marseille, Marseilles (FR)

( * ) Notice: Subject to any disclaimer, the term of this patent is extended or adjusted under 35 U.S.C. 154(b) by 0 days.

(21) Appl. No.: 16/320,259

(22) PCT Filed: Jun. 28, 2017

(86) PCT No.: PCT/EP2017/065971
§ 371 (c)(1),
(2) Date: Jan. 24, 2019

(87) PCT Pub. No.: WO2018/019507
PCT Pub. Date: Feb. 1, 2018

(65) Prior Publication Data
US 2019/0270949 A1    Sep. 5, 2019

(30) Foreign Application Priority Data
Jul. 28, 2016 (EP) .................................. 16305982

(51) Int. Cl.
*C11B 7/00* (2006.01)
*C11B 1/10* (2006.01)
*C12N 1/12* (2006.01)
*C11B 3/00* (2006.01)
*C12P 7/64* (2006.01)

(52) U.S. Cl.
CPC ............ *C11B 7/0008* (2013.01); *C11B 1/102* (2013.01); *C11B 1/104* (2013.01); *C11B 3/006* (2013.01); *C12N 1/12* (2013.01); *C12P 7/6409* (2013.01)

(58) Field of Classification Search
CPC ....... C11B 7/0008; C11B 1/102; C11B 1/104; C11B 3/2006; C12N 1/12; C12P 7/6409
USPC ........................................................ 554/205
See application file for complete search history.

(56) References Cited

U.S. PATENT DOCUMENTS

| | | |
|---|---|---|
| 2011/0263886 A1 | 10/2011 | Kale |
| 2013/0171721 A1 | 7/2013 | Knoshaug et al. |
| 2016/0053191 A1* | 2/2016 | Kwak ..................... C10L 1/026 44/388 |

FOREIGN PATENT DOCUMENTS

| | | |
|---|---|---|
| WO | 98/32819 A1 | 7/1998 |
| WO | 2012/078852 A2 | 6/2012 |

OTHER PUBLICATIONS

International Search Report issued in corresponding International Patent Application No. PCT/EP2017/065971 dated Aug. 2, 2017.
(Continued)

*Primary Examiner* — Deborah D Carr
(74) *Attorney, Agent, or Firm* — Morgan, Lewis & Bockius LLP

(57) ABSTRACT

The invention relates to a continuous process for fractionating a suspension chosen from a microalgal biomass or milk.

12 Claims, 1 Drawing Sheet

(56) References Cited

OTHER PUBLICATIONS

Figure 1:
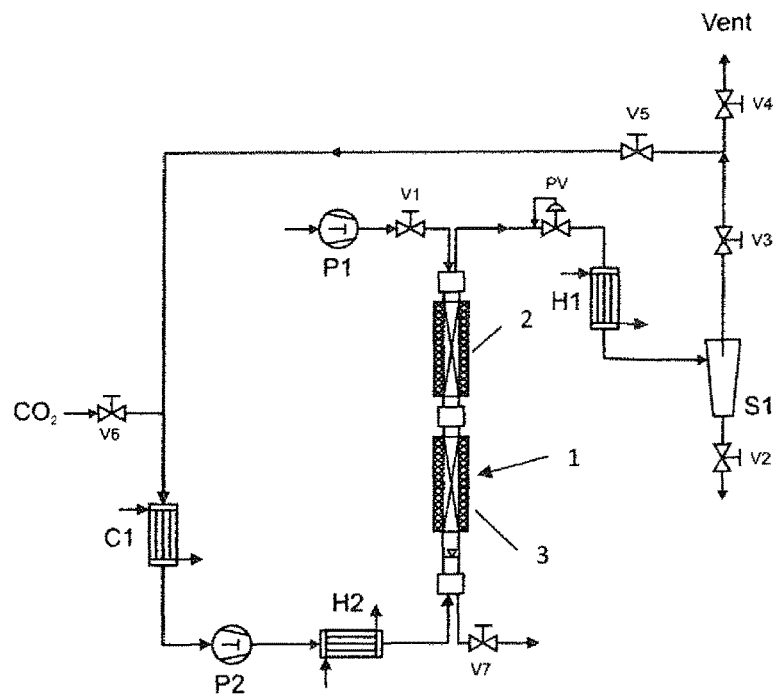

Written Opinion issued in corresponding International Patent Application No. PCT/EP2017/065971 dated Aug. 2, 2017.

* cited by examiner

CONTINUOUS PROCESS FOR FRACTIONATING A SUSPENSION

The invention relates to a continuous process for fractionating a suspension chosen from a microalgal biomass or milk.

Microalgal pastes comprise water in which are suspended microalgae (micron-sized cells) that are well known for containing neutral lipids, sometimes in significant amounts, among which glycerides and more particularly omega 3-fatty acids that can have a high-added value. Moreover, other high-added value compounds might be present, such as carotenoids (carotenes, like β-carotene, and xanthophylls, as for example astaxanthin and lutein) used as antioxidants, pigments or photoprotecting agents. Proteins, polymers and/or carbohydrates can also be recovered from microalgae for being valued.

It is why there is a great interest in a process for fractionating microalgal paste and recovering then neutral lipids and compounds of interest. The areas of application of these compounds are Energy (in particular biofuels), Nutraceuticals, Cosmetics, Pharmaceuticals, Human and Animal Food, materials, etc.

For example, WO 2012/078852 discloses a process for fractionating a biomass, in particular an algal biomass. This process comprises a first step, called "conditioning step", of conditioning the biomass for creating a disrupted cellular material. This conditioning step may be carried out by different methods among which a method in which the biomass is suspended in $CO_2$ and water.

Then a second step, called contacting step, is carried out. This stage consists in contacting the biomass with a non-polar solvent or a mixture of organic solvents having different polarities. This step is a liquid/liquid extraction step for solubilizing compounds soluble in the non-polar solvent and to retain the polar compounds in the aqueous phase of the algal biomass.

During the third step the phase containing the water-soluble compounds is separated from the phase containing the non-polar soluble compounds in the non-polar solvent.

After this step, the fourth step of the process aims to isolate the compounds of interest.

In this process, at least four main steps are carried out in a sequential manner and with numerous solvents in large quantity. Furthermore, this process is carried out in different chambers. This process is a batch process which does not allow to treat large quantities of biomass in a simple manner.

In contrast, the process of the invention is a continuous process enabling to fractionate large quantities of microalgal suspension. Furthermore, in the process of the invention, there is no need to disrupt the microalgal cells before fractionating and recovering the neutral lipids and the microalgal compounds of interest. Additionally, the process of the invention makes use of only one particular solvent, supercritical carbon dioxide ($CO_2$), except water coming from the wet microalgae biomass itself, for extracting lipids and compounds having a high added value.

Milk is a colloidal suspension containing neutral lipids in low but significant amounts, together with other compounds of interest. In this case also, there is a need for the fractionation of milk in a simple manner to obtain neutral lipids and compounds of interest. The areas of application of these compounds are in particular Human food, Cosmetics, Nutraceuticals.

For this aim, the present process for fractionating a suspension chosen from a microalgal biomass or milk is a single step process. The process consists in contacting the suspension with a supercritical fluid (supercritical $CO_2$), in a contactor.

The present invention thus concerns a process of fractionation of a suspension chosen from a microalgal biomass or milk, comprising the following steps:

a) contacting the suspension with a solvent consisting in supercritical $CO_2$ in a contactor, the suspension and the supercritical $CO_2$ being introduced in a counter current mode, b) continuously recovering a supercritical $CO_2$ rich phase exiting from the top of the contactor, after its contacting with the suspension, the supercritical $CO_2$ rich phase containing lipids extracted from the suspension, and a raffinate exiting from the bottom of the contactor, c) continuously separating the neutral lipids and/or the compounds of interest contained in the supercritical $CO_2$ rich phase, and the raffinate, d) the process comprising no step of disrupting the cells of the algal biomass before step a) is carried out.

Said neutral lipids are in particular chosen from triglycerides, diglycerides, monoglycerides, free fatty acids and their mixtures, the neutral lipids being in particular ω-3 fatty acids. These neutral lipids and in particular ω-3 fatty acids are of high added value.

By compounds of interest is in particular meant antioxidants, carbohydrates or pigments. Said compounds of interest are for instance carotenoids, in particular carotenes, like β-carotene, and/or xanthophylls, as for example astaxanthin and lutein.

When the suspension is a milk, compounds such as minerals (Ca, Na, K, P, . . . ), glucides and proteins are present in the raffinate and can be separated from water, for example by ultrafiltration.

By contactor is meant any device that enables a counter current extraction and the recovery of a top (lighter) phase and a bottom (heavier) phase.

In particular, the contactor is a fractionation column or a settler-mixer.

The wet microalgal biomass or the milk, and the supercritical $CO_2$ are introduced in a counter-current mode.

More precisely, the wet microalgal biomass or the milk (the feed) is introduced at the top of the fractionation column and the supercritical $CO_2$ is introduced at the bottom of the fractionation column. The two phases flows are induced by difference of gravity; the wet microalgal biomass or the milk constitutes the descending phase and the supercritical phase constitutes the ascending phase.

In particular, the suspension is a microalgal biomass.

The microalgal suspension may be the microalgal biomass as harvested (containing microalgae cells, water and potential waste particles). But, the microalgal biomass which is introduced in the fractionation column may also be the harvested microalgal biomass which has been previously concentrated, for example by centrifugation, filtration, or flocculation-flotation.

Thus, the wet microalgal biomass which is introduced in the fractionation column may have a concentration of microalgae comprised between 0.5 and 200 $g \cdot L^{-1}$, respectively corresponding to water content comprised between 99.95 and 80 wt %. In particular, these values are suitable on a lab, pilot or industrial scale.

In particular, the suspension is milk.

By milk is meant milk from animal or vegetal origin.

By milk from animal origin is meant the lacteal secretion of any mammal and milk products derived there from such as e.g. whole milk, partially skimmed milk, homogenized milk, pasteurized milk and liquid cream. In particular, the milk is chosen from cow, goat, sheep, buffalo and mare milk.

By milk from vegetal origin is meant plant milk. In particular, the milk is chosen from almond, cashew nut, nut, coca, rice, lupine, peanut, pea, oat, spelt, rye, quina, hemp, soy, sunflower and sesame milk.

The contacting step a) may be performed in presence of a polar modifier.

By polar modifier is meant a polar compound, which is soluble in supercritical carbon dioxide and increases the polarity of said supercritical carbon dioxide.

Polar modifiers are well known from the person skilled in the art and are in particular chosen from short chain alcohols.

By short chain alcohols is meant $C_1$-$C_4$ linear or branched alkanes substituted by one hydroxyl group, in particular methanol or ethanol.

The use of a polar modifier may enhance or even make possible the extraction of polar compounds of interest.

For example, when the suspension is a microalgual biomass and a polar modifier is used, some polar compounds may be solubilized in the fluid phase, as astaxanthin or lutein, and the β-caroten extraction may be enhanced.

In particular, the mass fraction of the polar modifier in the supercritical $CO_2$ phase is comprised from 0 to 20%.

By supercritical $CO_2$ phase is meant the supercritical $CO_2$ as defined in step a), and when present, the polar modifier and/or the esterification agent.

The contacting step a) may also be performed in presence of an esterification agent.

By esterification agent is meant a reactive compound or composition enabling the esterification of the neutral lipids bearing a carboxylic acid group.

Esterification agents are well known from the person skilled in the art and are in particular chosen from short chain alcohols; short chain alcohols and a catalyst chosen from acids and bases; dimethyl carbonate; a biocatalyst; and dimethyl carbonate and a biocatalyst.

By biocatalyst is in particular meant an enzyme catalyzing or performing the esterification reaction.

In particular, the esterification agent is methanol or ethanol, and optionally a base such as hydroxide or potassium hydroxide. The esterification agent may also be dimethyl carbonate and a biocatalyst such as Novozyme 435.

In presence of an esterification agent, which is mixed with the supercritical $CO_2$, both extraction and transesterification of lipids can be performed, leading to the extraction of fatty acids methyl esters—FAMEs—or fatty acids ethyl esters—FAEEs—, when said esterification agent is for instance methanol or ethanol respectively, in presence or not of a catalyst.

The transformation of neutral lipids into the corresponding esters enhances the separation since esters are more soluble in supercritical $CO_2$ than their corresponding lipids (glycerides or free fatty acids).

When short chain alcohols are mixed with the supercritical $CO_2$, they play the role of both a polar modifier and an esterification agent, depending on the concentration in alcohol.

Preferably, the process is carried out under pressure comprised between 8 and 30 MPa and at a temperature comprised between 35 and 70° C.

The pressure is below 30 MPa in order to ensure a certain difference between the densities of the encountered phases while allowing the solubilization of the neutral lipids and compounds of interest in the supercritical phase.

The pressure is below 70° C. in order to avoid the degradation of thermolabile compounds.

The massic ratio [flow rate of supercritical $CO_2$]/[flow rate of suspension] is preferably comprised between 2/1 and 250/1. In particular, these values are suitable whatever the column dimensions (height and internal diameter) of the contactor, more particularly on a lab, pilot or industrial scale.

The flow rate of supercritical $CO_2$ may be comprised between 3 and 20 kg·h$^{-1}$ and the flow rate of suspension may be comprised between 0.08 and 1.5 kg·h$^{-1}$ for a two meters high column with an internal diameter of about 20 mm. These values are particularly suitable on a lab scale.

The flow rate of supercritical $CO_2$ may be of about 50 kg·h$^{-1}$ and the flow rate of suspension may be of about 5 kg·h$^{-1}$ for a 4 meters high column with an internal diameter of about 58 mm. These values are particularly suitable on a pilot scale.

The flow rate of supercritical $CO_2$ may be of about 600 kg·h$^{-1}$ and the flow rate of suspension may be of about 50 kg·h$^{-1}$ for a 8 meters high column with an internal diameter of about 126 mm. These values are particularly suitable on an industrial scale.

When the contactor is a fractionation column, the contact between the feed and the supercritical phase may be enhanced by the use of a packing in the fractionation column. Indeed, the fractionation column which is used is preferably a packed fractionation column. Packed fractionation columns enable to increase the contact area between the encountered phases, allowing then a good mass transfer.

In particular, the packing of the fractionation column is chosen among random packings and structured packings, more particularly the ones respectively sold under the trademark Interpack® or Sulzer®.

An example of a packing appropriate for the fractionation column is a random packing sold under the trademark Interpack® 10 mm. This packing has a specific area of 580 m$^2$/m$^3$.

Another example of packing is a structured packing commercialized under the trademark Sulzer® CY, which can be used for industrial columns.

The Interpack® packing 10 mm is a packing made of metal (stainless steel).

The packing Sulzer® CY is a packing made of hybrid gauze material.

Thanks to the high contact area between the two phases and thanks to the specific properties of mass transfer of supercritical fluids, $CO_2$ diffuses easily in the bulk of the microalgal paste or the milk and more especially inside the microalgal cells, thus extracting the most soluble compounds. The fact that the microalgal biomass is in suspension in water will help the transfer of the different solutes through the wet, soft and potentially swollen cell membranes.

The pressure and the temperature to be applied during the process depend on the solubility of the compounds to be extracted from the suspension chosen from a microalgal biomass or milk by supercritical $CO_2$. For example, a good solubilization of neutral (non-polar) lipids is obtained at 60° C. and 30 MPa.

Furthermore, the pressure and the temperature to be used when carrying out the process of the invention also depend on the difference between the density of the suspension chosen from a microalgal biomass or milk and the density of supercritical $CO_2$. This difference should not be lower than 150 kg·m$^{-3}$.

The phases exiting from the top and from the bottom of the fractionation column flow naturally by difference of gravity. The top phase which is the extract (or lighter phase) contains mainly supercritical $CO_2$ plus neutral lipids (and/or other high-added value compounds), and low amounts of water extracted from the suspension. The bottom phase is generally called the raffinate (or heavier phase). The bottom phase is composed mainly of water, microalgae cells, waste particles and low amounts of $CO_2$, in the case of a microalgal biomass, and mainly of water, solid material (glucides, proteins, minerals, etc.) and low amounts of $CO_2$, in the case of milk.

The two phases (top and bottom phases) are continuously collected by simple depressurization.

When exiting from the fractionation column the top and bottom phases come back to a lower pressure (than the fractionation pressure) or directly to ambient pressure.

When set to ambient pressure, supercritical $CO_2$ comes back to gaseous state and the targeted compounds are spontaneously separated from the $CO_2$. The top phase is depressurized and $CO_2$ is separated from the liquid remaining phase so-called extract collected in a separator. The extract is mainly composed of neutral lipids (tri-, di- and monoglycerides as well as of Free Fatty Acids), some of them being high-added value compounds (ω-3 fatty acids), and, when the suspension is a microalgal biomass, of pigments and/or lipophilic antioxidants. The extract may contain low amounts of water. $CO_2$ may be recycled with a recycling rate for example of 98%.

The bottom phase is depressurized and $CO_2$ (contained in rather small amounts) is separated from the liquid remaining phase so-called raffinate. The raffinate contains large amounts of water, microalgae cells (when the suspension is a microalgal biomass) and the different compounds non-soluble in supercritical $CO_2$.

The separation between the extract and the raffinate, and supercritical $CO_2$ is spontaneous and easily performed by a simple depressurization.

At the top of the column, one or several separators can be used. Several separators with different conditions of pressure and temperature may allow a selective separation of the extracted compounds. As for an example, triglycerides or ω-3 fatty acids compounds can be separated from pigments. In that case, the pressure decreases sequentially from the first separator to the following ones. The less soluble compounds will be recovered in the first separator while the most soluble compounds will be collected in the last separator.

The use of a gradient of pressure along several separators is well known from the person skilled in the art and is in particular described by Michel Perrut in "*Extraction par fluide supercritique*", j2770, Techniques de l'Ingénieur, 1999.

The raffinate phase can be submitted to decantation to separate the microalgae cells from the aqueous liquid phase.

The fractionation column may comprise several sections in which different temperatures may be applied. The induced internal reflux may enhance the separation. In that case, the feed may not be introduced at the top of the column but at the middle or between the middle and the top. The pressure would be preferentially set between 8 and 20 MPa. Indeed, for such conditions of pressure, the retrograde behavior is observed. That means that the solute solubility in supercritical $CO_2$ decreases when the temperature increases. Thus, if the top section is at a higher temperature than the other lower ones, the solute solubilized in the supercritical phase in the lowest sections, will condense (since they will be less soluble at a higher pressure) creating then an internal reflux.

The use of a gradient of temperature along several sections of a contactor, in particular a fractionation column, is well known from the person skilled in the art and is in particular described by Michel Perrut (ibid.).

In order to have the process of the invention better understood, an example of a carrying it out is given below. This example is not limitative and only illustrative of the process of the invention.

FIGURES

FIG. 1 is a schematic diagram of a laboratory-scale fractionation unit that may be used in the process of the invention. This fractionation unit includes a packed column noted 1, with an internal diameter of 19 mm and 2 m height with a viewing cell (not represented) located at the bottom of column 1, below the solvent (supercritical $CO_2$) injection nozzle (not represented). The temperature of column 1 is controlled by means of two independent heating jackets, noted 2 and 3.

C1: cooler; H1, H2: heaters; P1, P2: High-pressure pumps, S1: separator; PV: back-pressure regulator; V1-V7: valves—(1) column; (2), (3): column sections.

Figure 2:
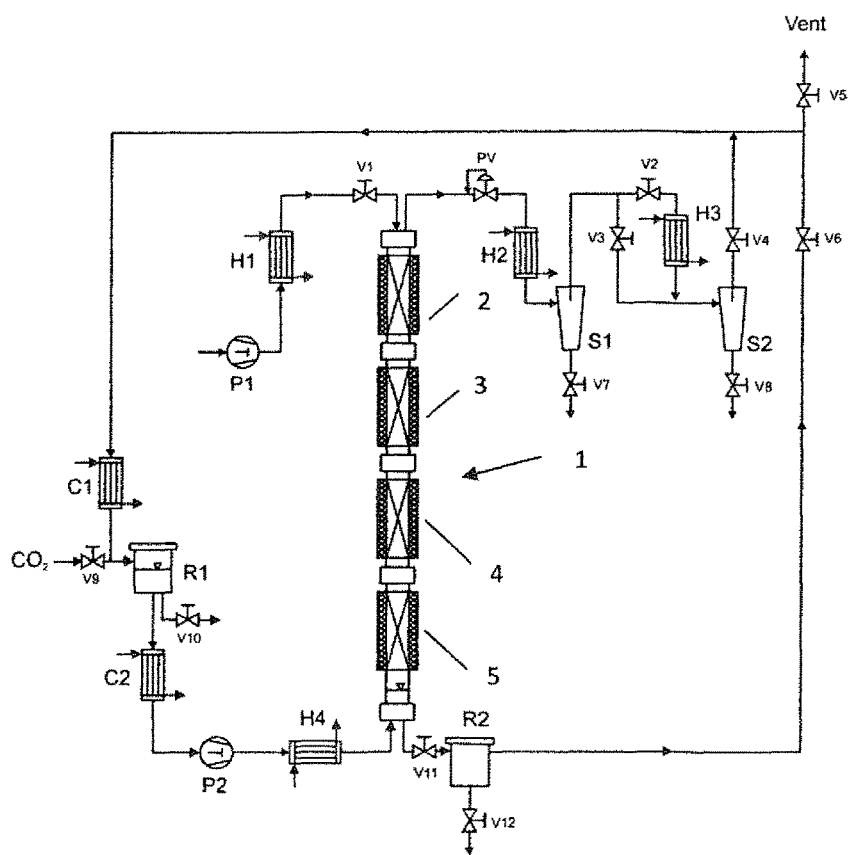

FIG. 2 is a schematic diagram of a pilot or industrial-scale fractionation unit that may be used in the process of the invention. This fractionation unit includes a packed column noted 1. The temperature of column 1 is controlled by means of four independent heating jackets, noted 2-5.

C1, C2: coolers; H1-H4: heaters; P1, P2: High-pressure pumps, S1,S2,R2: separators; R1: buffer tank; PV: back-pressure regulator; V1-V12: valves—(1) column; (2)-(5) column sections.

EXAMPLE 1: SUPERCRITICAL FRACTIONATION OF NEUTRAL LIPIDS (MAINLY TRIGLYCERIDES AND FATTY ACIDS) FROM A MACROALGAL SUSPENSION

The process of the invention will be described in reference to FIG. 1 annexed which is a schematic diagram of a fractionation unit used in the process of the invention.

This fractionation unit includes a packed column noted 1 in FIG. 1, with an internal diameter of 19 mm and 2 m height with a viewing cell (not represented) located at the bottom of column 1, below the solvent (supercritical $CO_2$) injection nozzle (not represented).

The column is able to withstand pressures up to 30 MPa, and its temperature (from 35 to 70° C.) is controlled by means of two independent heating jackets, noted 2 and 3 in FIG. 1. The column is filled with 10 mm Interpack® random packings from VFF (Germany), with a measured apparent density of 588 kg m$^{-3}$, a specific surface area of 580 m$^{-1}$ and a void fraction (equivalent porosity) of 0.917 in order to improve mass transfer efficiency.

During operation, carbon dioxide which is introduced through a valve noted V6 in FIG. 1, under 4.5 MPa is cooled to 278 K (5° C.) in a double tube heat exchanger, noted C1 in FIG. 1, before being pumped and then heated to the working temperature, by a heater noted H2 in FIG. 1. A high-pressure piston pump, noted P2 in FIG. 1, from Separex (France) with a top capacity of 15 Lh$^{-1}$ of liquid carbon dioxide and a maximum attainable pressure of 35 MPa delivers the supercritical $CO_2$ at the suitable flow rate. In this example, the working temperature is 60° C. and the working pressure is 25 MPa. Those conditions allow the recovery of neutral lipids with high separation efficiency.

However, the temperature may vary from 35 to 70° C. and the pressure may vary from 10 to 30 MPa.

The $CO_2$-over-feed ratio in the present example varies between 20 and 150 corresponding to a $CO_2$ flow rate set at 12 kg h$^{-1}$ and feed flow rate varying from about 0.08 up to 0.55 kg h$^{-1}$.

However, this $CO_2$ flow rate may vary from 5 to 15 kg h$^{-1}$.

When supercritical $CO_2$ leaves column 1, the overhead current is depressurized through a backpressure regulator, noted PV in FIG. 1, to recover the extract in a pressurized cyclonic separator, noted S1 in FIG. 1. The extract is heated using the heater H1 placed between the exit of the column and the separator to ensure to maintain the desired temperature.

The $CO_2$ rich phase is no longer a supercritical fluid, it is then recycled and condensed into the cooler C1 to reduce carbon dioxide consumption.

If the separation between the extracted compounds and $CO_2$ is not complete, an additional apparatus may be used in order to purify the $CO_2$ rich phase. For example, activated carbon may be used to ensure the complete gas separation.

In this example, the concentration of the algal biomass is of 100 g L$^{-1}$.

However, this concentration may vary from 0.5 to 200 g L$^{-1}$.

The liquid mixture which is fed by a Gilson 307 HPLC piston pump, noted P1 in FIG. 1, which has a 20 mL min$^{-1}$ (about 1.2 kg h$^{-1}$) maximum capacity, through a value noted V1 in FIG. 1.

The supercritical $CO_2$ flow rate is controlled by a Rheonik® RHE 14 mass flowmeter (Germany) (not represented in FIG. 1), while the algal biomass feed flow rate is directly controlled by the pump P1 speed.

The extract containing neutral lipids and the raffinate are collected from the bottom of the cyclonic separator S1 and of column 1, respectively, by manual regulation of the corresponding valves, noted V2 and V7 in FIG. 1.

The microalgal biomass is introduced in the top of column 1 via a pump noted P1, and a valve noted V1 in FIG. 1.

The supercritical solvent (supercritical $CO_2$) is introduced at the bottom of the column (1).

Thus, the supercritical $CO_2$ and the algal biomass flow in the column at counter-current. Supercritical $CO_2$ solubilizes all or part of the neutral lipids and/or the products with a high added value such as pigments or antioxidants. If pure carbon dioxide is used, the neutral lipids are the most soluble compounds and will be then preferentially be "extracted" from the algal cells. Those neutral lipids can be tri-, di- or monoglycerides as well as free fatty acids. Even if pure supercritical $CO_2$ is used, since water can act as a co-solvent, β-caroten can also be solubilized in the light phase. If a polar modifier (ethanol, for instance) is added to supercritical $CO_2$, some more polar compounds will be solubilized in the fluid phase, as astaxanthin or lutein, and the β-caroten extraction will be enhanced.

The algal biomass, from which the neutral lipids and the compounds of interest have been extracted, is recovered at the bottom of the column through a valve, noted V7 in FIG. 1.

In the present case, since feed flow rate varies from 0.08 up to 0.55 kg h$^{-1}$, a quantity of neutral lipids varying from 16 to 100 g can be recovered after one hour of production for a biomass containing 20 wt % (of dry matter) of neutral lipids and for a complete recovery. Those quantities can be as high as 10 kg (of neutral lipids) per hour of production at a larger scale, for example with a 8 m high column and with an internal diameter of 126 mm.

When supercritical $CO_2$ is depressurized, it returns to its gaseous state so that the oil containing the lipids and any compounds of interest are spontaneously separated.

In the present case, the oil contained 20 wt % (of dry matter) of neutral lipids and up to 2 wt % (of dry matter) of polar compounds (antioxidants).

The glycerides (tri-, di- and mono-), the free fatty acids, antioxidants and the other compounds of interest can be separated from each other.

The triglycerides are separated from the antioxidants using different separators with different conditions of pressure and temperature. As for example, the operating conditions of the first separator may be set at 20 MPa and 40° C. allowing the recovery of pigments. The operating conditions of the second separator may be set at 6 MPa and 40° C. allowing the recovery of glycerides.

EXAMPLE 2: DELIPIDATION OF MILK

Depending on its origin, milk is constituted of about 87% of water and 13% of dry extract. The dry extract represents about 130 g·L$^{-1}$ and contains on the average of 35-45 g of fat. About 98.5% of fat fraction are simple lipids in suspension: 95-96% are triglycerides, 3% are diglycerides, the rest are monoglycerides.

Since the water content and the composition of neutral lipids are almost the same for milk and microalgae suspension, the apparatus, method and operating conditions presented in example 1 can be applied for both types of feed.

As for example, the working temperature in the column is fixed at 60° C. and the working pressure is 25 MPa.

The $CO_2$-over-feed mass ratio in the present example (for ex. for a 2 m high column) varies between 20 and 150 corresponding to a $CO_2$ flow rate set at 12 kg·h$^{-1}$ and feed flow rate varying from 0.08 up to 0.55 kg·h$^{-1}$.

The extract is constituted of the totality of neutral lipids and the raffinate contains water and solid material (glucides, proteins, minerals, . . . ). The separation of dry matter and water can be performed by ultrafiltration.

The invention claimed is:

1. A process of fractionation of a suspension chosen from a microalgal biomass or milk, comprising the following steps:
    a) contacting the suspension with a solvent consisting in supercritical $CO_2$ in a contactor, the suspension and the supercritical $CO_2$ being introduced in a counter current mode,
    b) continuously recovering a supercritical $CO_2$ rich phase exiting from the top of the contactor, after its contacting with the suspension, the supercritical $CO_2$ rich phase containing lipids extracted from the suspension, and a raffinate exiting from the bottom of the contactor,
    c) continuously separating the neutral lipids and/or the compounds of interest contained in the supercritical $CO_2$ rich phase, and the raffinate,
    d) the process comprising no step of disrupting the cells of the algal biomass before step a) is carried out.

2. The process of claim 1, wherein the suspension is a microalgal biomass, said microalgal biomass having a concentration of microalgae comprised between 0.5 and 200 g·L$^{-1}$ of microalgae.

3. The process of claim 1, wherein the suspension is milk, said milk being from animal or vegetal origin.

4. The process of claim 1, wherein the contactor is a fractionation column, in particular a packed fractionation column, or a settler-mixer.

5. The process of claim 4, wherein the packing of the fractionation column is chosen among random packings and structured packings.

6. The process of claim 1, wherein the fractionation is carried out at a pressure comprised between 8 and 30 MPa and at a temperature comprised between 35 and 70° C.

7. The process of claim 1, carried out with the massic ratio [flow rate of supercritical $CO_2$]/[flow rate of suspension] comprised between 2/1 and 250/1.

8. The process of claim 1, carried out with:
   the flow rate of supercritical $CO_2$ comprised between 3 and 20 kg $h^{-1}$ and the flow rate of suspension comprised between 0.08 and 1.5 kg $h^{-1}$;
   the flow rate of supercritical $CO_2$ of about 50 kg $h^{-1}$ and the flow rate of suspension of about 5 kg $h^{-1}$; or
   the flow rate of supercritical $CO_2$ of about 600 kg $h^{-1}$ and the flow rate of suspension of about 50 kg $h^{-1}$.

9. The process of claim 1, where the separated supercritical $CO_2$ is recirculated in the fractionation column.

10. The process of claim 1, wherein the neutral lipids are chosen from triglycerides, diglycerides, monoglycerides, free fatty acids and their mixtures, the neutral lipids being in particular ω-3 fatty acids.

11. The process of claim 1, wherein the compounds of interest antioxidants, carbohydrates or pigments.

12. The process of claim 1, wherein the contacting step a) is performed in presence of a polar modifier and/or an esterification agent.

\* \* \* \* \*